US005663117A

United States Patent [19]
Warner

[11] Patent Number: 5,663,117
[45] Date of Patent: Sep. 2, 1997

[54] ALKOXYLATED PRIMARY ALCOHOL SURFACTANTS PROVIDING ENHANCED EFFICACY AND/OR RAINFASTNESS TO GLYPHOSATE FORMULATIONS

[75] Inventor: James M. Warner, St. Louis, Mo.

[73] Assignee: Monsanto Company, St. Louis, Mo.

[21] Appl. No.: 664,476

[22] Filed: Jun. 17, 1996

Related U.S. Application Data

[63] Continuation-in-part of Ser. No. 491,466, Jun. 16, 1995, abandoned, which is a continuation-in-part of Ser. No. 341,501, Nov. 22, 1994, abandoned, which is a continuation-in-part of Ser. No. 169,805, Dec. 17, 1993, abandoned.

[51] Int. Cl.⁶ ........................... A01N 25/24; A01N 25/30; A01N 57/04
[52] U.S. Cl. ........................... 504/206; 71/DIG. 1
[58] Field of Search ........................... 504/206

[56] References Cited

U.S. PATENT DOCUMENTS

| | | | |
|---|---|---|---|
| 4,990,175 | 2/1991 | Petroff et al. | 71/92 |
| 5,078,782 | 1/1992 | Nielsen et al. | 71/100 |
| 5,118,444 | 6/1992 | Nguyen | 252/390 |
| 5,258,354 | 11/1993 | Tack | 503/227 |
| 5,258,359 | 11/1993 | Kassebaum et al. | 504/206 |

FOREIGN PATENT DOCUMENTS

| | | | |
|---|---|---|---|
| B-38389/89 | 1/1990 | Australia | A01N 25/30 |
| 0 274 369 | 7/1988 | European Pat. Off. | A01N 57/20 |
| 0 290 416 | 11/1988 | European Pat. Off. | A01N 25/30 |

OTHER PUBLICATIONS

Brumbaugh, E. H., *Third International Symposium on Adjuvants for Agrochemicals*, Cambridge, U.K., (Aug. 1992). *Abstract.

Wyrill et al., "Glyphosate Toxicity to Common Milkweed and Hemp Dogbane as Influenced by Surfactants," *Weed Science* (1977), vol. 25, Issue 3, pp. 275–287.

*Primary Examiner*—S. Mark Clardy
*Attorney, Agent, or Firm*—Arnold, White & Durkee

[57] ABSTRACT

Alcohol surfactants such as ethoxylated Guerbet alcohol, are added to composition containing other surfactants to enhance the efficacy and/or rainfastness of herbicidal compositions containing glyphosate or its salts. They compositions of the invention may be in the form of concentrated compositions that are storage stable and water soluble or diluted solutions that can be directly applied to foliage.

26 Claims, No Drawings

ALKOXYLATED PRIMARY ALCOHOL SURFACTANTS PROVIDING ENHANCED EFFICACY AND/OR RAINFASTNESS TO GLYPHOSATE FORMULATIONS

RELATED INVENTIONS

The present application is a continuation-in-part application of Ser. No. 08/491,466 filed Jun. 16, 1995, now abandoned which is a continuation-in-part application of Ser. No. 08/341,501 filed Nov. 22, 1994, now abandoned, which is a continuation-in-part application of Ser. No. 08/169,805, filed Dec. 17, 1993, now abandoned.

FIELD OF THE INVENTION

This invention comprises a new method of use of relatively low-cost, agriculturally acceptable surfactants to enhance the efficacy or rainfastness of foliar-applied pesticidal and plant growth modifying agents. This invention further comprises new and useful compositions of such agents, in particular the herbicide N-phosphonomethylglycine or its salts or mixtures thereof, containing such efficacy- or rainfastness-enhancing surfactants.

BACKGROUND OF THE INVENTION

Foliar-applied pesticidal and plant growth modifying chemicals are widely used in agricultural, industrial, recreational and residential areas worldwide. These chemical agents illustratively include insecticides, fungicides, herbicides, plant growth regulators and plant nutrients among other chemicals. Such chemicals are typically applied by spraying on the foliage of vegetation to be protected, controlled, killed or modified, but other methods such as rope-wick application are known. Some of these agents show contact action, killing, controlling or modifying the growth of target organisms at the site of deposition. Other chemicals are systemic, translocating within the plant to a site of action remote from the site of deposition. Still other chemicals show both contact and systemic action.

A common concern with several such chemicals is that efficacy can be reduced if rain falls shortly after spraying or other mode of application. This concern is more pronounced with chemicals that have moderate to high solubility in water. Many methods of overcoming the problem of reduced efficacy due to rain have been disclosed. Such methods are said to have the aim of enhancing "rainfastness" of foliar-applied agents.

Methods to enhance rainfastness include addition to the spray solution of oils or other lipophilic substances, polymers and other materials which are alleged to enhance spreading and sticking of the applied formulation to leaves, and addition of various surfactants. Among surfactants which have been disclosed for rainfastness enhancement are organosilicone copolymers, for example the ethoxylated siloxane Silwet L-77 of Union Carbide Corporation. Such surfactants, as well as other spray additives used to enhance rainfastness, tend to be relatively expensive and many have other drawbacks.

Alternatively, a rainfastness enhancing material may be provided by the manufacturer or supplier of the foliar-applied pesticidal or plant growth modifying agent as an ingredient in the formulation of said agent.

An example of a foliar-applied agent whose efficacy is sensitive to the occurrence of rain shortly after application is the herbicide N-phosphono-methylglycine, also known by its common name glyphosate.

Glyphosate is a highly effective and commercially important herbicide useful for combating the presence of a wide variety of unwanted vegetation, including agricultural weeds. Glyphosate is applied as a formulated product to the foliage of annual and perennial grasses and broadleaf plants and the like, and is taken up over a period of time into the leave whence it translocates throughout the plant.

Glyphosate in ionic form has relatively high water solubility, especially when formulated as a salt, and during the uptake period immediately after application glyphosate is vulnerable to being washed off the foliage by rain or by overhead watering or irrigation. As glyphosate has practically no herbicidal activity in the soil, its efficacy is seriously reduced by such washing.

The length of time during which glyphosate is somewhat vulnerable to rain depends on many environmental and plant factors, and on the duration and intensity of rain, but can be as short as thirty minutes or as long as twelve hours or more after application. In the great majority of cases rain falling six or more hours after application does not seriously affect performance of the herbicide.

Usually, glyphosate is formulated in commercial compositions in the form of a water-soluble salt. Salts in commercial use include alkylamine salts, such as the isopropylamine salt, alkali metal salts, such as the sodium salt, the ammonium salt and the trimethylsulfonium salt. However, formulations of glyphosate in its acid form are also used. Typical glyphosate salt formulations include aqueous concentrates, requiring simple dilution in water for application by the end-user, and water-soluble or water-dispersible dry formulations, especially granules, requiring dissolution or dispersion in water prior to application. Most formulations, whether liquid or dry, also contain one or more surfactants. Even with such surfactants in the formulation there remains a need for enhanced rainfastness of glyphosate in many situations.

The ethoxylated siloxane surfactant Silwet L-77 referred to above has been the subject of much published research into rainfastness enhancement for glyphosate salt formulations. Its main active ingredient is 1,1,1,3,5,5,5-heptamethyltrisiloxanylpropyl-omega-methoxypoly (ethylene oxide) where the average number of ethylene oxide units is approximately seven. Other siloxanes of related composition are also described in the art. In addition to the high cost of Silwet L-77, common to all siloxanes, a number of disadvantages have been described, notably its tendency to antagonize the activity of glyphosate on some species in the absence of rain. A technical solution to this problem is provided in Australian Patent No. 609,628, wherein a humectant such as glycerin added to the spray solution overcomes the antagonism; however cost still remains a major deterrent in most situations.

A major advance in cost-effective rainfastness enhancement for glyphosate was provided in U.S. Pat. No. 5,258,354, wherein acetylenic diol surfactants, exemplified by ethoxylates of 2,4,7,9-tetramethyl-5-decyne-4, 7-diol, are shown to give rainfastness at least equal to Silwet L-77 when used in the presence of certain other surfactants, but without the occurrence of antagonism in the absence of rain. Concentrate formulations of glyphosate with such acetylenic diol surfactants are disclosed which are both chemically and physically stable over a wide range of conditions.

While acetylenic diol surfactants are obtainable at much lower cost than effective organosilicone surfactants, they could still be too costly for many applications. In most cases the end-user wishes some degree of insurance against the possibility of rain washing the herbicide off the foliage before it has had time to penetrate into the leaves. The end-user seldom knows that it will certainly rain. For such insurance purposes, economics dictate a still lower-cost adjuvant or formulation ingredient. Various low-cost surfactants have from time to time been died to give rainfastness enhancement, including ethoxylated alkylphenols such as octylphenol and nonylphenol ethoxylates. These are among the most widely used general purpose adjuvants for glyphosate in many markets, and are not considered by most users to provide reliable rainfastness enhancement.

E. H. Brumbaugh (Third International Symposium on Adjuvants for Agrochemicals, Cambridge, U.K., August 1992) showed that addition of APSA-80, a product said to contain 80% of a nonionic surfactant based on nonoxynol-9 (nonylphenol ethoxylate with an average of 9 moles ethylene oxide per mole of nonlphenol), enhanced rainfastness of glyphosate, applied as Roundup® herbicide in an ultra-low volume of water (30.6 l/ha). The adjuvant was used at concentrations ranging from 0.1% to 0.5% of the spray solution. Rainfastness improvement was not evident on all species.

There is provided herein a new method of use of alcohol alkoxylate surfactants of molecular structure defined more particularly below for enhancing the rainfastness of foliar-applied pesticidal and plant growth modifying agents.

There are also provided herein new, storage-stable, liquid or dry concentrate compositions comprising glyphosate or one or more of its salts, an alcohol alkoxylate surfactant of molecular structure defined below and one or more other surfactants, said compositions showing enhanced rainfastness by comparison with similar compositions not containing said alcohol alkoxylate surfactant, and showing at least equal rainfastness by comparison with much higher-cost compositions of the prior art based on ethoxylated siloxane or acetylenic diol surfactants. Not all alcohol alkoxylate surfactants provide the desired degree of rainfastness enhancement. Alcohol alkoxylates of molecular structure defined below, when used in accordance with the present invention, give superior rainfastness by comparison with, for example, primary linear alcohol alkoxylates or alkylphenol alkoxylates of the prior art.

Also provided herein are new, storage-stable liquid or dry concentrate compositions comprising glyphosate or one or more of its salts, an alcohol alkoxylate surfactant of molecular structure defined below and one or more other surfactants, said compositions showing enhanced herbicidal efficacy by comparison with glyphosate compositions known in the art, whether rain occurs shortly after application or not.

Among the surfactants used in combination with alcohol alkoxylates in compositions of the present invention are ethoxylated tertiary and quaternary alkylamines and alkylamine oxides.

It is known in the art that ethoxylated alkylamine or alkylamine oxide surfactants having an average alkyl chain length in the range from 10 to 20 carbon atoms and having an average of from 2 to 20 moles of ethylene oxide (EO) per mole of amine, are effective in potentiating the herbicidal activity of glyphosate compositions. European Patent No. 0 290 416, for example, discloses glyphosate compositions containing tertiary alkylamine surfactants within the range encompassed by the above description, and notes that such compositions, particularly those with EO levels in the lower part of the range mentioned above, have high herbicidal unit activity. European Patent No. 0 274 369 discloses highly efficacious glyphosate compositions containing quaternary alkylamine surfactants within the range encompassed by the above description. In both cases it is disclosed that for best performance the compositions should also contain a significant mount of an inorganic ammonium salt such as ammonium sulfate.

U.S. Pat. No. 5,118,444 discloses ethoxylated alkylamine oxide surfactants within the range encompassed by the above description, and indicates their usefulness as components of glyphosate formulations.

Ammonium sulfate is bulky and can only be accommodated in a concentrate formulation at an effective level by greatly lowering the content of active ingredient, in this case glyphosate. A significant advance in the art of formulating glyphosate concentrates would result from identification of a material which further enhances the efficacy of compositions containing ethoxylated alkylamine surfactants, but which is effective at a lower concentration than is required in the case of ammonium sulfate. That material could be incorporated in a concentrate formulation without unacceptable dilution of the glyphosate active ingredient. The present invention provides just such an advance in the art.

SUMMARY OF THE INVENTION

There is provided a new method, for enhancing the efficacy or rainfastness of foliar-applied pesticidal and plant growth modifying agents, using alcohol alkoxylate surfactants such as those having the representative chemical structure

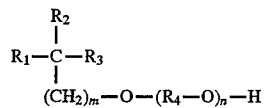

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups, m is a positive integer from 1 to 3 and n is an average number from about 3 to about 30.

There are also provided new, storage-stable, liquid or dry concentrate compositions comprising (a) glyphosate or one of its agriculturally acceptable salts, (b) one or more alcohol surfactants such as those having the representative chemical structure.

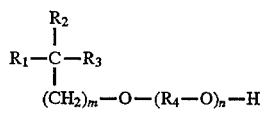

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups, m is a positive integer from 1 to 3 and n is an average number from about 3 to about 30, and (c) one or more other surfactants. In preferred compositions, $R_3$ in the structure of the alcohol surfactant is hydrogen and $R_4$ is ethylene.

Compositions of the invention possess at least one of the following benefits over compositions known in the art. (1) They may show enhanced rainfastness by comparison with similar compositions not containing said alcohol surfactants, and at least substantially equal rainfastness by comparison with much higher-cost compositions of the prior art based on ethoxylated siloxane or acetylenic diol surfactants. (2) They may show enhanced herbicidal efficacy, even in the absence of rain, by comparison with similar compositions not containing said alcohol surfactants.

A method of use of such compositions to provide acceptable control of weeds and other unwanted vegetation whether or not rain falls shortly after application is also provided.

DETAILED DESCRIPTION OF THE INVENTION

In the most widely used commercial glyphosate compositions, the herbicide glyphosate is formulated as its isopropylamine salt. Excellent control of most plant species can normally be obtained at rates of 0.1 to 10 kg/ha of glyphosate-isopropylamine. It is generally preferred to refer to the mount of glyphosate applied in terms of glyphosate acid equivalent, conventionally abbreviated as "a.e.". Application to plants is most commonly done by spraying a solution of the glyphosate herbicide in water.

For most applications, the efficacy of glyphosate is significantly improved by the presence of a surfactant. However, not all surfactants are equally effective in improving the herbicidal activity of glyphosate, and some surfactants are quite ineffective or may even reduce glyphosate activity. Among the most effective prior art surfactants for improving glyphosate activity are alkoxylated alkylamine surfactants, including both tertiary and quaternary amine types. Nonionic surfactants differ widely and to a large extent unpredictably in their ability to enhance glyphosate activity. The alcohol alkoxylates of the present invention are relatively weak in this regard, when used as the sole surfactant.

Most commercial glyphosate salt formulations already contain one or more surfactants, most commonly of the tertiary or quaternary alkylamine alkoxylate class mentioned above. For example, Roundup® herbicide of Monsanto Company is an aqueous concentrate formulation of the isopropylamine salt of glyphosate. In addition to glyphosate in the amount of 360 grams a.e./liter, Roundup herbicide as sold, for example, in Canada contains a surfactant based on ethoxylated tallowamine having an average of about 15 moles EO per mole of amine.

The end-user may add more surfactant to a glyphosate spray solution; as well as amines, low-cost nonionic surfactants of the ethoxylated primary linear alcohol, alkylphenol or fatty acid classes are especially widely used in this way. However, because of the wide variation in efficacy of such surfactants it is generally preferred to include an effective surfactant in the concentrate formulation. In addition to the relatively poor efficacy of alcohol alkoxylates when used as the sole surfactants with glyphosate, these alcohol surfactants suffer the further drawback that they cannot be formulated with glyphosate salts in agriculturally useful amounts in aqueous concentrates, except in the presence of compatibilizing agents. Such agents include a wide variety of tertiary and quaternary amine surfactants, alkyl polyglycosides and other materials.

There is now provided a new method, for enhancing the efficacy or rainfastness of foliar-applied pesticidal and plant growth modifying agents, using alcohol alkoxylate surfactants such as those having the representative chemical structure:

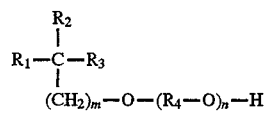

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups, m is positive integer from 1 to 3 and n is an average number from about 3 to about 30, preferably from about 7 to about 14, and most preferably from about 9 to about 12. $R_1$ and $R_2$ are preferably straight-chain alkyl groups with a total of about 10 to about 20 carbon atoms, $R_3$ is preferably hydrogen, $R_4$ is preferably ethylene and m is preferably 1.

There are also provided new, storage-stable, liquid or dry concentrate compositions comprising (a) glyphosate or one of its agriculturally acceptable salts, (b) one or more alcohol surfactants such as those having the representative chemical structure:

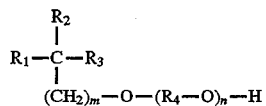

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups, m is positive integer from 1 to 3 and n is an average number from about 3 to about 30, and (c) one or more other surfactants, said compositions showing enhanced efficacy and/or rainfastness by comparison with similar compositions not containing said alcohol surfactants, and showing at least substantially equal rainfastness by comparison with much higher-cost compositions of the prior art based on ethoxylated siloxane or acetylenic diol surfactants.

A method of use of such compositions to provide acceptable control of weeds and other unwanted vegetation whether or not rain falls shortly after application is also provided.

A particular embodiment of this invention is a surfactant composition comprising (a) an alcohol surfactant in which $R_3$ is hydrogen, $R_1$ and $R_2$ are straight chain alkyl groups with a total of about 10 to about 20 carbon atoms, $R_4$ is ethylene, m is 1 and n is an average number in the range from about 7 to about 14, most preferably from about 9 to about 12; and (b) an ethoxylated tertiary or quaternary alkylamine or alkylamine oxide surfactant having an average of from about 2 to about 20 moles of ethylene oxide per mole of amine. Said surfactant composition may be coformulated with a glyphosate herbicide in an aqueous or dry concentrate formulation. Alternatively, said surfactant composition may be provided to the end user separately from the glyphosate herbicide, for tank mixing by him immediately prior to application.

Typically in commercial preparations of secondary alcohol surfactants the ethoxylated alcohol group can be located anywhere on the alkyl chain except at the ends, and such preparations are therefore mixtures of alcohols. The alkyl chain length also normally varies within commercial preparations.

In the examples that follow, one such preparation is referred to as "$C_{11-15}$ secondary alcohol 9 EO". This product has a total of about 11 to about 15 carbon atoms in the alkyl chain and an average of about 9 moles ethylene oxide per mole of alcohol (n=9). $C_{11-15}$ secondary alcohol ethoxylates such as this are commercially available from Union Carbide Corporation as the Tergitol 15-S series.

An example of preferred surfactant which has been found useful according to the present invention has the representative chemical structure:

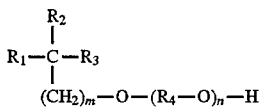

wherein $R_1$ and $R_2$ are straight chain alkyl groups with a total of about 10 to about 20 carbon atoms, $R_3$ is hydrogen, $R_4$ is ethylene, m is 1 and n is an average number in the range from about 7 to about 14. Such surfactants may be produced by reacting ethylene oxide, according to methods known in the art, with alcohols known in the art as "Guerbet alcohols".

To provide the desired rainfastness enhancement of a foliar applied pesticidal or plant growth modifying agent, alcohol alkoxylates of the invention may be used at concentrations in the spray solution in the range from about 0.05 to about 2 percent by volume, preferably from about 0.1 to about 1 percent by volume, although in certain circumstances greater or lesser concentrations may be used.

In concentrate or ready-to-use glyphosate formulations, the alcohol alkoxylate surfactant may usefully be included at weight/weight ratios of said surfactant to glyphosate a.e. from about 1:20 to about 1:1, preferably from about 1:12 to about 1:2 and most preferably from about 1:6 to about 1:3.

In ready-to-use formulations, glyphosate is typically present at about 0.5 to about 2 percent a.e. by weight. Aqueous concentrate formulations of the invention may contain about 5 to about 40 percent glyphosate a.e. by weight.

Dry concentrate formulations of the invention may contain about 10 to about 75 percent glyphosate a.e. by weight. Preferred dry concentrate formulations are water-soluble granules containing about 40 to about 70 percent glyphosate a.e. by weight.

Preferred glyphosate salts for use in aqueous or dry formulations of the invention include ammonium, alkylamine, for example isopropylamine, alkylsulfonium, for example trimethylsulfonium, and alkali metal salts. Most commonly these salts have a molar ratio of actions to glyphosate artions in the range from about 1:1 to about 2:1.

Long-term shelf stability is an important commercial attribute of concentrate formulations of pesticidal and plant growth modifying agents. In the case of aqueous concentrate formulations, such as those of glyphosate, it is particularly important that surfactants in the formulation do not separate from the other ingredients as a distinct phase. Many such aqueous concentrates show a tendency for phase separation at high temperatures. The minimum temperature at which such phase separation occurs is known as the "cloud point" of the formulation. It is well known to those of skill in the art that most nonionic surfactants, ethoxylated alcohols being a good example, have rather poor compatibility with high ionic strength solutions such as aqueous concentrate formulations of glyphosate salts. This poor compatibility is manifested as a low cloud point, leading to unacceptably poor shelf stability of the formulation.

In accordance with the present invention alcohol alkoxylates are incorporated at useful levels in an aqueous concentrate formulation of glyphosate salt by further including in the formulation a compatibilizing agent which raises the cloud point of the formulation to an acceptable level, for example 50° C. or higher.

In both aqueous and dry concentrate glyphosate formulations where rainfastness enhancement is desired, additional surfactant(s) should be included in an amount sufficient to provide acceptable herbicidal efficacy in the absence of rain, and to allow the alcohol alkoxylate to exhibit the desired level of rainfastness enhancement.

The amount of such additional surfactant other than alcohol alkoxylate to be included depends greatly on the chemical composition of that surfactant, on the plant species targeted and on environmental factors. Normally, however, the weight/weight ratio of alcohol alkoxylate to the total of other surfactants is in the range from about 1:20 to about 5:1, preferably from about 1:10 to about 2:1 and most preferably from about 1:5 to about 1.1.

The surfactant(s) additional to alcohol alkoxylates in glyphosate compositions of the invention may be selected from alkyl monoglycosides, alkyl polyglycosides, sucrose alkylesters, secondary, tertiary, or quaternary alkylamine alkoxylates, non-alkoxylated tertiary or quaternary alkylamines, alkylamine oxides, alkylbetaines and the like. Good results may be obtained, for example, with cocoamine 2 EO and 5 EO (e.g. Ethomeen C/12 and C/15, Akzo Chemicals Inc.), N-methyltallowammonium chloride 5 EO, 10 EO and 15 EO, N-methyloctadecylammonium chloride 15 EO (e.g. Ethoquad 18/25, Akzo Chemicals Inc.)., N-methylcocoammonium chloride 2 EO (formulated at 35% concentration in water as Ethoquad C/12W, Akzo Chemicals Inc.), N-methylcocoammonium chloride 15 EO (e.g. Ethoquad C/25, Akzo Chemicais Inc.), N,N-diethyl-N-methylammonium chloride 1 EO+7PO (Eracol CC-9, Witco Corporation), N, N-dimethyldodecylamine (Armeen DM 12D, Akzo Chemicals Inc.), N,N,N-trimethylcocoammonium chloride (formulated at 33% concentration in water as Arquad C-33W, Akzo Chemicals Inc.), N,N,N-trimethyltallowammonium chloride (formulated at 27% concentration in water as Arquad T-27W, Akzo Chemicals Inc.), potassium laurylbetaine, alkyl polyglucosides (Agrimul PG 2067 and Agrimul PG 2069, Henkel Corporation), $C_{8-10}$ alkyl monoglucoside, and sucrose cocoate (Crodesta SL-40, Croda Inc.).

Several of the Examples herein utilize N-methylcocoammonium chloride with 2 moles ethylene oxide ("cocoamine quat 2 EO") as the additional surfactant. Other Examples herein utilize tertiary cocoamine or tallowamine with 5 moles ethylene oxide ("cocoamine 5 EO" or "tallowamine 5 EO" respectively) as the additional surfactant.

In addition to glyphosate or its salts, the alcohol alkoxylate and the additional surfactant(s), any of a variety of further ingredients or adjuvants may be included in formulations of the present invention as long as such added materials are not significantly antagonistic to the glyphosate herbicidal activity and/or to the alcohol alkoxylate efficacy or rainfastness-enhancing activity. Mixtures of glyphosate with other herbicides are also within the scope of the present invention. Examples of such other herbicides include bialaphos, glufosinate, 2,4-D, MCPA, dicamba, diphenylethers, imidazolinones and sulfonylureas.

Methods of use of some glyphosate formulations are well known to those of skill in the art. Aqueous concentrate formulations of the invention are diluted in an appropriate volume of water and applied, for example by spraying, to the weeds or other unwanted vegetation to be killed or controlled. Dry concentrate formulations of the invention are dissolved or dispersed in an appropriate volume of water and applied in the same way.

The present invention is illustrated by but not limited to the following Examples. In describing concentrate compositions of the Examples, percentages are given by weight unless otherwise indicated. In describing concentrations of surfactants in spray solutions, percentages are given by volume.

EXAMPLES

Comparative herbicidal activity with and without simulated rain was determined in greenhouse and field tests. For greenhouse tests, seeds or propagules of selected species were planted in 10.2 cm square pots of soil with added fertilizer. Temperature and relative humidity were allowed to fluctuate within limits defined for each test described in the following Examples. Plants were allowed to grow until the desired growth stage or size (defined for each test) for spraying. Pots were selected for uniformity before treatment and three replicate pots were assigned to each treatment. Spray solutions were prepared by dilution or dissolution of concentrate herbicide formulations in water. When desired to test "tank mix" application of surfactant compositions, these were added to other spray solution at the required concentration. Spraying was performed with a device which simulates agricultural field spraying equipment, delivering a fine spray at a pressure of about 207 kilopascals. Speed of travel of the spray device over the plants was adjusted to give the desired spray volume (defined for each test). For logistical reasons, all three replicates of each treatment were sprayed together. "Rain" treatments were applied by repeated passage of a coarse spray of water over the plants at some desired period of time after herbicide spraying. The amount and duration of "rain" were noted. After spraying and "rain" treatment, the plants were returned to the greenhouse. Herbicidal efficacy was evaluated by visual assessment at one or more selected time periods after treatment and recorded as "percent control" on an arbitrary scale by comparison with untreated plants. On this scale 0 means no visible effect and 100 means death of all plants. In the Examples, percent control values given are the means of three replicates.

In field tests, treatments were applied post-emergence to plants which had grown naturally or from seeds planted mechanically in rows. A randomized block design with three replicates was used, with plot size depending on local circumstances. A backpack sprayer with multiple nozzles giving an overlapping spray pattern was used to maximize uniformity of application. "Rain" was simulated by means of overhead irrigation equipment tested for uniformity of deposition of water. Percent control was evaluated in similar fashion to that described above for greenhouse tests.

Example 1

The following surfactant adjuvants were tested for rainfastness enhancement of glyphosate in a field.
Prior Art
1. Triton AG-98

2. 2,4,7,9-tetramethyl-5-decyne-4,7-diol 10 EO
Invention
3. $C_{11-15}$ secondary alcohol 9 EO
4. Adjuvant 3+cocoamine quat 2 EO (1:1 ratio)

In this and other Examples, a number followed by "EO" refers to the average moles of ethylene oxide per mole of surfactant.

Glyphosate was applied as the isopropylamine salt, either without surfactant (the glyphosate formulation sold as Accord® herbicide by Monsanto Company) or with a surfactant based on tallowamine ethoxylate (the glyphosate formulation sold as Roundup® herbicide by Monsanto Company). Triton AG-98 (Union Carbide Corporation) is a widely used low foam commercial agricultural adjuvant, 80% of which is octylphenol ethoxylate.

A total of 11 grass and broadleaf species were planted in rows:

A. *Panicum dichotomiflorum* (fall panicum, PANDI)

B. *Lolium sp.* (annual ryegrass, LOLSS)

C. *Bromus tectorum* (downy brome, BROTE)

D. *Sorghum vulgare* (grain sorghum cv. Rox Orange, SORGR)

E. *Echinochloa crus-galli* var. *frumentae* (Japanese millet, ECHCF)

F. *Echinochloa crus-galli* (barnyardgrass, ECHCG)

G. *Setaria faberi* (giant foxtail, SETFA)

H. *Abutilon theophrasti* (velvetleaf, ABUTH)

I. *Chenopodium album* (common lambsquarters, (CHEAL).

J. *Kochia scoparia* (kochia, KCHSC)

K. *Salsola kali* (Russian thistle, (SASKR)

All applications were made at a spray volume of 10 gallons/acre (93.5 l/ha). To minimize variation in rain-free period, all plots were sprayed within 15 minutes. Rain was simulated by overhead irrigation using an array of fixed sprinklers, which were turned on minutes after the midpoint of the 15-minute glyphosate application period. The sprinklers were left on for 60 minutes, targeting a "rainfall" of at least 0.5 inch (12 mm). Gauges located throughout the experimental area showed that the actual amount of "rain" delivered varied from 11 to 18 mm, with a mean of 14.5 mm.

Data in Table 1 show percent inhibition as recorded 15 days after treatment (DAT) with glyphosate at the rate of 0.25 lb. a.e./acre (0.28 kg a.e./ha), without and with "rain" described above. For all "rain" treatments the adjuvants were applied at a concentration of 0.25% in the spray solution. For the "no rain" treatments, adjuvant 4 was applied at 0.25%, but the other adjuvants were applied, through operator error, at 0.125%. This error does not affect any of the conclusions drawn below from this test.

TABLE 1

Percent inhibition 15 DAT without and with simulated rain (means of 3 replicates).
Adjuvants 1–4 and species A–K as defined in text.

| Glyphosate product | Adjuvant | Rain | Species |   |   |   |   |   |   |   |   |   |   |
|---|---|---|---|---|---|---|---|---|---|---|---|---|---|
|   |   |   | A | B | C | D | E | F | G | H | I | J | K |
| Roundup ® | None | no | 86 | 96 | 98 | 95 | 67 | 53 | 100 | 88 | 90 | 81 | 62 |
|   |   | yes | 8 | 28 | 20 | 32 | 22 | 12 | 84 | 32 | 10 | 12 | 10 |
| Roundup ® | 1 | no | 87 | 100 | 100 | 88 | 73 | 68 | 100 | 80 | 92 | 80 | 91 |
|   |   | yes | 13 | 37 | 42 | 48 | 28 | 15 | 96 | 33 | 28 | 17 | 18 |
| Roundup ® | 2 | no | 82 | 100 | 100 | 90 | 85 | 72 | 100 | 88 | 94 | 88 | 75 |
|   |   | yes | 20 | 50 | 50 | 58 | 40 | 15 | 98 | 40 | 38 | 30 | 33 |

TABLE 1-continued

Percent inhibition 15 DAT without and with simulated rain (means of 3 replicates).
Adjuvants 1–4 and species A–K as defined in text.

| Glyphosate product | Adjuvant | Rain | A | B | C | D | E | F | G | H | I | J | K |
|---|---|---|---|---|---|---|---|---|---|---|---|---|---|
| Roundup ® | 3 | no | 85 | 89 | 100 | 94 | 83 | 80 | 100 | 79 | 92 | 87 | 87 |
|  |  | yes | 20 | 57 | 75 | 56 | 37 | 25 | 96 | 38 | 42 | 20 | 20 |
| Roundup ® | 4 | no | 96 | 99 | 100 | 99 | 84 | 77 | 100 | 73 | 93 | 90 | 77 |
|  |  | yes | 18 | 48 | 73 | 57 | 35 | 15 | 94 | 42 | 37 | 25 | 28 |
| Accord ® | 4 | yes | 13 | 59 | 58 | 67 | 42 | 22 | 98 | 42 | 37 | 25 | 28 |

The results of this test show Adjuvant 3 (containing a secondary alcohol ethoxylate) to provide significant rainfastness enhancement of Roundup. While not giving complete rainfastness under the severe conditions of this test, the use of Adjuvant 3 nevertheless gave greater enhancement of rainfastness than the Triton AG-98 (Adjuvant 1 of the prior art) and was at least as effective overall as 2, 4, 7, 9-tetramethyl-5-decyne-4, 7-diol 10 EO (Adjuvant 2 of the prior art) which is a much higher-cost material. Adjuvant 4 provided a similar degree of rainfastness enhancement to Adjuvant 3, and when added to the surfactantless product Accord gave similar performance with "rain" as when added to the surfactant-containing product Roundup.

Example 2

Aqueous concentrate formulations of the isopropylamine salt of glyphosate were prepared at a glyphosate a.e. loading of 18.4% (equivalent to about 200 g a.e./liter). All contained 7% cocoamine quat 2 EO and 10.2% nonionic surfactant. The nonionic surfactant was selected from several secondary alcohol ethoxylates; Silwet L-77, 2, 4, 7, 9-tetramethyl-5-decyne-4, 7-diol 10 EO, nonylphenol 8 EO, 10 EO and 12 EO and $C_{12-15}$ primary alcohol 7 EO, 9 EO and 12 EO. These formulations were tested for rainfastness in a greenhouse test.

The test species was *Panicum maximum* (guineagrass, PANMA). All glyphosate formulations were applied at 1.5 lb a.e./acre (1.68 kg a.e./ha) in a spray volume of 20 gallons/acre (185 l/ha). Commercial Roundup herbicide was included as a standard. Simulated rain was applied in the amount of 6 mm over a period of 15 minutes, beginning 1 hour after glyphosate treatment. Data on percent inhibition without and with "rain" are presented in Table 2.

TABLE 2

Percent inhibition of guineagrass 15 DAT without and with simulated rain (means of 3 replicates).

| Roundup ® herbicide (standard) Nonionic in formulation: | No rain 100 | Rain 65 |
|---|---|---|
| Silwet L-77 | 100 | 70 |
| 2,4,7,9-tetramethyl-5-decyne-4,7-diol 10 EO | 98 | 94 |
| nonylphenol 8 EO | 100 | 97 |
| nonylphenol 10 EO | 100 | 81 |
| nonylphenol 12 EO | 100 | 63 |
| $C_{12-15}$ primary alcohol 7 EO | 99 | 90 |
| $C_{12-15}$ primary alcohol 9 EO | 98 | 81 |
| $C_{12-15}$ primary alcohol 12 EO | 99 | 68 |
| $C_{11-15}$ secondary alcohol 7 EO | 100 | 89 |
| $C_{11-15}$ secondary alcohol 9 EO | 100 | 99 |

TABLE 2-continued

Percent inhibition of guineagrass 15 DAT without and with simulated rain (means of 3 replicates).

| Roundup ® herbicide (standard) Nonionic in formulation: | No rain 100 | Rain 65 |
|---|---|---|
| $C_{11-15}$ secondary alcohol 12 EO | 100 | 86 |
| $C_{11-15}$ secondary alcohol 15 EO | 99 | 80 |
| $C_{12}$ branched secondary alcohol 6 EO | 100 | 66 |
| $C_{12}$ branched secondary alcohol 10 EO | 100 | 98 |

In this test, acceptable performance (>85% inhibition) with rain was obtained with 2, 4, 7, 9-tetramethyl-5-decyne-4, 7-diol 10 EO of the prior art, and with two lower cost materials, nonylphenol 8 EO and $C_{12-15}$ primary alcohol 7 EO, likewise outside the scope of the present invention. It will be noted that even a slight increase in the EO level on either the nonylphenol or the primary alcohol significantly reduced the rainfastness of the formulation; at the 12 EO level no rainfastness advantage at all was obtained with either of these surfactant types. By contrast, $C_{11-15}$ secondary alcohol surfactants gave enhanced rainfastness over a wide range of EO levels. Of the $C_{12}$ branched secondary alcohol surfactants tested, the 10 EO example gave excellent rainfastness while the 6 EO example did not give significant rainfastness enhancement in this test.

Example 3

Aqueous concentrate formulations of the isopropylamine salt of glyphosate were prepared at a glyphosate a.e. loading of 31% (equivalent to about 360 g a.e./liter). All contained 7.5% cocoamine quat 2 EO and 8.6% nonionic surfactant. Formulations contained as the nonionic $C_{11-15}$ secondary alcohol 9 EO or $C_{12}$ branched secondary alcohol 10 EO; for comparison, other formulations were made containing nonionic disclosed as rainfastness aids in the prior art such as 2, 4, 7, 9-tetramethyl-5-decyne-4, 7-diol 10 EO or nonylphenol 8 EO. These formulations were tested for rainfastness in a greenhouse test.

The test species was *Elymus repens* (quackgrass, AGRRE). All glyphosate formulations were applied at both 0.75 and 1.5 lb. a.e./acre (0.84 and 1.68 kg a.e./ha) in a spray volume of 20 gallons/acre (187 l/ha). Commercial Roundup herbicide was included as a standard. Simulated rain was applied in the amount of 6 mm over a period of 15 minutes, beginning 1 hour after glyphosate treatment. Data on percent inhibition without and with "rain" are presented in Table 3.

TABLE 3

Percent inhibition of quackgrass 28 DAT without simulated rain (means of 3 replicates).

| Application rate lb/a (kg/h) | 0.75 (0.84) | | 1.5 (1.68) | |
|---|---|---|---|---|
| | No rain | Rain | No Rain | Rain |
| Roundup (standard) | 73 | 30 | 92 | 72 |
| Nionionic in formulation: | | | | |
| 2,4,7,9-tetramethyl-5-decyne-4,7-diol 10 EO | 94 | 78 | 98 | 94 |
| nonylphenol 8 EO | 97 | 83 | 98 | 79 |
| $C_{11-15}$ secondary alcohol 9 EO | 93 | 96 | 100 | 98 |
| $C_{12}$ branched secondary alcohol 10 EO | 94 | 84 | 100 | 88 |

At the lower glyphosate rate, both formulations containing secondary alcohols gave better rainfastness than the formulation of the prior art containing 2, 4, 7, 9-tetramethyl-5-decyne-4, 7-diol 10 EO, and the formulation of the invention containing $C_{11-15}$ secondary alcohol 9 EO gave better rainfastness than either of the prior art formulations. At the higher glyphosate rate, both formulations of the present invention gave better rainfastness than the formulation of the prior art containing nonylphenol 8 EO, and gave comparable rainfastness to the much higher cost formulation containing 2, 4, 7, 9-tetramethyl-5-decyne-4,7 diol 10 EO.

Considering Examples 2 and 3 together, it is clear that $C_{11-15}$ secondary alcohol 9 EO and $C_{12}$ branched secondary alcohol 10 EO of the present invention are more consistent in their rainfastness enhancing performance than nonylphenol ethoxylates of the prior art.

Example 4

The following glyphosate formulations were tested for herbicidal activity and rainfastness by comparison with Roundup® herbicide in a field trial;

Formulation A: 31% glyphosate a.e. as the isopropylamine salt, 7.5% cocoamine quat 2 EO, 8.6% nonylphenol 8 EO.

Formulation B: 31% glyphosate a.e. as the isopropylamine salt, 7.5% cooamine quat 2 EO, 8.6% $C_{11-15}$ secondary alcohol 9 EO.

A total of 7 grass and broadleaf species were planted in rows:

L. *Digitaria ciliaris* (southern crabgrass, DIGSP)

M. *Brachiaria platyphylla* (broadleaf signalgrass, BRAPP)

N. *Sorghum halepense* (johnsongrass, SORHA)

O. *Echinochloa crus-galli* (barnyardgrass, ECHCG)

P. *Sida spinosa* (prickly sida, SIDSP)

Q. *Echinochloa crus-galli* var. *frumentae* (Japanese millet, ECHCF)

R. *Sesbania exaltata* (hemp sesbania, SEBEX)

All applications were made at a spray volume of 10 gallons/acre (93.5 l/ha). To minimize variation in rain-free period, all plots were sprayed within 15 minutes. Rain was simulated by overhead irrigation using a lateral move irrigation system, which was turned on 60 minutes after the midpoint of the 15-minute glyphosate application period to give a "rainfall" of approximately 0.5 inch (12 mm).

Data in Table 4 show percent inhibition as recorded 21 days after treatment (DAT) with glyphosate at the rate of 0.75 lb. a.e./acre (0.84 kg a.e./ha), without and with "rain" as described above.

TABLE 4

Percent inhibition 21 DAT without and with simulated rain (means of 3 replicates). Formulations A and B and species L–R as defined in text.

| Formulation | Rain | Species | | | | | | |
|---|---|---|---|---|---|---|---|---|
| | | L | M | N | O | P | Q | R |
| Roundup (standard) | no | 98 | 95 | 99 | 86 | 75 | 90 | 77 |
| | yes | 65 | 57 | 86 | 52 | 65 | 78 | 68 |
| A | no | 100 | 93 | 99 | 87 | 77 | 89 | 69 |
| | yes | 79 | 70 | 93 | 62 | 68 | 82 | 75 |
| B | no | 100 | 92 | 95 | 79 | 73 | 89 | 72 |
| | yes | 87 | 75 | 96 | 68 | 77 | 84 | 82 |

Examples 5–7

In Examples 5–7, a short-term whole plant assay was used to evaluate relative efficacy of aqueous glyphosate compositions containing tallowamine 5 EO and either $C_{11-15}$ secondary alcohol 9 EO or a Guerbet alcohol in different concentrations and proportions relative to one another.

The following procedures were used for testing in Examples 5–7. This test is designed to give an indication of relative rainfastness of different glyphosate compositions. Equal volumes of uniformly sized seeds (20–25 in number) of barley cv. Pennco were sown in a growing medium consisting of a 3:2:1 sand/soil/peat mixture in 4 inch square plastic pots. Pots were placed in a controlled environment growth chamber providing a 14 hour photoperiod, day and night temperatures of 78° F. and 66° F. respectively, and a relative humidity in the range from 30% to 50%. Light was provided by a combination of metal halide and sodium vapor lamps. All pots were bottom watered at 1200 hr on the first day, resulting in rapid saturation of the growing medium. Seedling emergence occurred on the third and fourth days. On the seventh day, all pots were fertilized by bottom watering with a Peters 20-20-20 fertilizer containing 475 ppm soluble nitrogen.

On the eighth day, pots were sorted into 6 replicate blocks according to plant size. Treatments, including no-treatment controls, were randomly assigned within each block, one treatment per pot.

Plants were treated with glyphosate compositions in rapid succession between 0830 hr and 0900 hr on the ninth day, when average plant height was 13–15 cm and the second leaf was just beginning to elongate. Compositions were applied using a calibrated single-nozzle track sprayer delivering 187 l/ha through a Teejet 8001E nozzle at 276 kilopascals. Plants were removed from the growth chamber immediately before treatment and returned to the same growth chamber immediately after treatment. Pots were spatially arranged in a randomized complete block experimental design. At 6 hours after treatment, plants in all pots were timed by cutting to 20 mm above the top edge of the pot. This removed approximately 90% of the barley leaf area. Pots were bottom watered once daily for the remainder of the study. Data collection took place on the sixteenth day, 7 days after treatment.

Average height of barley regrowth in each pot was measured to the nearest 5 mm increment, from the earlier cutting height 20 mm above the edge of the pot. All plants in each pot were then cut at 20 mm above the edge of the pot and total fresh weight was recorded.

Example 5

All compositions in this Example contained glyphosate as the isopropylamine salt at a concentration calculated to deliver 0.42 kg a.e./ha. Polyoxyethylene tallowamine 5 EO (T/Am 5) concentration was varied independently of $C_{11-15}$ secondary alcohol 9 EO (S/A1 9) concentration as will be clear from the tables below. Untreated plants had a mean regrowth height of 175 min.

| T/Am 5 | S/A1 9 (% w/v) | | | | | |
|---|---|---|---|---|---|---|
| (% w/v) | 0 | 0.15 | 0.3 | 0.45 | 0.6 | 0.75 |
| Mean height of regrowth (mm) | | | | | | |
| 0 | 148 | 101 | 112 | 124 | 120 | 122 |
| 0.05 | 149 | 52 | 39 | 51 | 55 | 66 |
| 0.1 | 64 | 51 | 49 | 51 | 60 | 63 |
| 0.15 | 65 | 53 | 50 | 47 | 46 | 52 |
| 0.2 | 58 | 50 | 45 | 52 | 54 | 52 |
| 0.25 | 57 | 47 | 45 | 43 | 47 | 42 |
| Least significant difference (P = 0.05) 15 | | | | | | |
| Mean fresh weight of regrowth (g) | | | | | | |
| 0 | 1.92 | 1.24 | 1.34 | 1.46 | 1.43 | 1.45 |
| 0.05 | 1.80 | 0.70 | 0.54 | 0.61 | 0.77 | 0.90 |
| 0.1 | 0.83 | 0.75 | 0.68 | 0.69 | 0.80 | 0.80 |
| 0.15 | 0.78 | 0.68 | 0.72 | 0.65 | 0.61 | 0.67 |
| 0.2 | 0.73 | 0.61 | 0.62 | 0.71 | 0.68 | 0.66 |
| 0.25 | 0.76 | 0.56 | 0.56 | 0.59 | 0.68 | 0.61 |
| Least significant difference (P = 0.05) 0.20 | | | | | | |

In this study, when S/A1 9 was the sole surfactant, the lowest tested concentration (0.15%) was the most effective in potentiating glyphosate activity, there being a slight tendency for performance to deteriorate as concentration was increased above this level. When T/Am 5 was the sole surfactant, the lowest tested concentration (0.05%) gave little or no improvement in glyphosate efficacy, but a concentration of 0.1% gave very significant improvement. 1% further improvement was seen as T/Am 5 concentration was increased above 0.1%.

When T/Am concentration was 0.1% or higher, adding S/A1 9 gave little further improvement in glyphosate efficacy in this study. However, at 0.05% T/Am 5, addition of S/A1 9 gave a response far in excess of any response that could have been predicted from the weak performance of S/A1 9 alone. This study therefore clearly shows a synergistic interaction between S/A1 9 and T/Am 5 at suboptimal levels of T/Am 5.

Example 6

A further study was conducted to focus greater attention on low T/Am 5 concentrations and to try to confirm a synergistic interaction between T/Am 5 and S/A1 9 at such low T/Am 5 concentrations. Glyphosate rates in this study were also lower (0.07, 0.14 and 0.28 kg a.e./ha). All compositions in this Example contained glyphosate as the monoisopropylamine salt. T/Am 5 concentration was again varied independently of S/A1 9 concentration as will be clear from the tables below, in which results for all three glyphosate rates are averaged. Untreated plants had a mean regrowth height of 168 mm.

| T/Am 5 | S/A1 9 (% w/v) | | | | | |
|---|---|---|---|---|---|---|
| (% w/v) | 0 | 0.031 | 0.062 | 0.125 | 0.25 | 0.5 |
| Mean height of regrowth (mm) | | | | | | |
| 0 | 171 | 144 | 145 | 151 | 156 | 165 |
| 0.016 | 124 | 87 | 88 | 91 | 93 | 120 |
| 0.031 | 118 | 90 | 84 | 85 | 93 | 99 |

-continued

| T/Am 5 | S/A1 9 (% w/v) | | | | | |
|---|---|---|---|---|---|---|
| (% w/v) | 0 | 0.031 | 0.062 | 0.125 | 0.25 | 0.5 |
| 0.062 | 123 | 92 | 79 | 79 | 79 | 98 |
| 0.125 | 116 | 92 | 88 | 86 | 84 | 85 |
| 0.25 | 113 | 84 | 85 | 75 | 73 | 78 |
| Least significant difference (P = 0.05) 11 | | | | | | |
| Mean fresh weight of regrowth (g) | | | | | | |
| 0 | 2.83 | 2.16 | 2.28 | 2.31 | 2.44 | 2.98 |
| 0.016 | 1.82 | 1.32 | 1.24 | 1.33 | 1.40 | 1.90 |
| 0.031 | 1.64 | 1.46 | 1.33 | 1.25 | 1.32 | 1.51 |
| 0.062 | 1.75 | 1.44 | 1.18 | 1.28 | 1.18 | 1.47 |
| 0.125 | 1.72 | 1.39 | 1.36 | 1.34 | 1.37 | 1.32 |
| 0.25 | 1.71 | 1.32 | 1.32 | 1.19 | 1.21 | 1.28 |
| Least significant difference (P = 0.05) 0.20 | | | | | | |

As in the previous study (Example 15), when S/A1 9 was the sole surfactant, the lowest tested concentration, in this case just 0.03 1%, was the most effective in potentiating glyphosate activity, there being once again a slight tendency for performance to deteriorate as concentration was increased above this level. When T/Am 5 was the sole surfactant, all concentrations, even as low as 0.016% , gave significant improvement in glyphosate efficacy. No significant further improvement was seen as T/Am 5 concentration was increased above 0.016%.

Adding S/A1 9 to T/Am 5 improved glyphosate efficacy beyond that achievable with T/Am 5 alone. In this study, the improvement was seen with all combinations except for combinations of high S/A1 9 and T/Am 5 concentration. In most cases addition to T/Am 5 of S/A1 9 gave a response far in excess of any response that could have been predicted from the weak performance of S/A1 9 alone. This study therefore confirms the synergistic interaction between S/A1 9 and T/Am 5.

Comparisons may be drawn between certain 1:1 combinations of S/A1 9 and T/Am 5 and either S/A1 9 alone or T/Am alone at the same total surfactant concentration as shown in the following table.

| Total surfactant concentration | T/Am 5 alone | 1:1 Combination | S/A1 9 alone |
|---|---|---|---|
| 0.062 | 1.75 | 1.46 | 2.28 |
| 0.125 | 1.72 | 1.18 | 2.31 |
| 0.25 | 1.71 | 1.34 | 2.44 |

In all cases the fresh weight reduction is greater with the combination of surfactants than with either surfactant alone at the same total concentration.

Example 7

Aqueous formulations of glyphosate as the isoproplyamine salt containing T/Am, an ethoxylated Guerbet alcohol, and a 50/50 weight % blend of these surfactants were prepared. Various such ethoxylated Guerbet alcohols have been included in formulations of this type, having the following representative chemical structure:

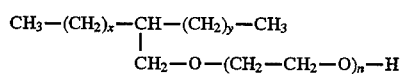

They include one example G1 in which x+y is 8 and n is an average of 7.7, and another example G2 in which x+y is 12 and n is an average of 9.0. The formulations of this example were combined with aqueous solution of isopropyl amine salt of glyphosate and the resulting solution was further diluted with water to produce a spray solution. The spray solution was sprayed on plants in a greenhouse to determine their herbicidal efficacy.

Compositions containing glyphosate with tallowamine, glyphosate with Guerbet alcohol surfactant, and glyphosate with a Guerbet alcohol surfactant/tallowamine blend were applied at three different dosages to barley plants. The percentage inhibition was then recorded in terms of net inhibition of vertical growth (VG) and net inhibition of fresh weight (FW). The following results were obtained:

|  | tallowamine | | Guerbet | | blend | |
|---|---|---|---|---|---|---|
|  | VG | FW | VG | FW | VG | FW |
| 1. Guerbet - G2 total surfactant = 0.0625% | | | | | | |
| glyphosate 0.0625 lb/acre | 18 | 15 | 10 | 18 | 20 | 20 |
| glyphosate 0.125 lb/acre | 29 | 37 | −5 | 3 | 37 | 44 |
| glyphosate 0.25 lb/acre | 53 | 50 | 20 | 25 | 67 | 61 |
| 2. Guerbet - G2 total surfactant = 0.125% | | | | | | |
| glyphosate 0.0625 lb/acre | 9 | 8 | 4 | −1 | 26 | 28 |
| glyphosate 0.125 lb/acre | 45 | 49 | −1 | 5 | 35 | 42 |
| glyphosate 0.25 lb/acre | 65 | 63 | 25 | 26 | 61 | 55 |
| 3. Guerbet - G2 total surfactant = 0.25% | | | | | | |
| glyphosate 0.0625 lb/acre | 20 | 16 | 8 | 13 | 28 | 30 |
| glyphosate 0.125 lb/acre | 41 | 34 | −5 | 7 | 58 | 53 |
| glyphosate 0.25 lb/acre | 60 | 61 | 18 | 20 | 69 | 64 |
| 4. Guerbet - G1 total surfactant = 0.0625% | | | | | | |
| glyphosate 0.0625 lb/acre | 12 | 12 | −2 | −5 | 24 | 27 |
| glyphosate 0.125 lb/acre | 37 | 35 | 7 | 16 | 54 | 50 |
| glyphosate 0.25 lb/acre | 54 | 53 | 28 | 29 | 65 | 53 |
| 5. Guerbet - G1 total surfactant = 0.0125% | | | | | | |
| glyphosate 0.0625 lb/acre | 17 | 19 | 4 | −6 | 19 | 15 |

-continued

|  | tallowamine | | Guerbet | | blend | |
|---|---|---|---|---|---|---|
|  | VG | FW | VG | FW | VG | FW |
| glyphosate 0.125 lb/acre | 10 | 18 | 1 | 3 | 47 | 41 |
| glyphosate 0.25 lb/acre | 44 | 47 | 23 | 20 | 67 | 61 |
| 6. Guerbet - G1 total surfactant = 0.25% | | | | | | |
| glyphosate 0.0625 lb/acre | 20 | 19 | −3 | −16 | 28 | 28 |
| glyphosate 0.125 lb/acre | 23 | 21 | 2 | 13 | 36 | 32 |
| glyphosate 0.25 lb/acre | 41 | 42 | 14 | 16 | 59 | 58 |

Example 8

This experiment was conducted to determine greenhouse efficacy of Guerbet alcohol surfactants in combination with T/Am 5 as potentiators for glyphosate as the isopropylamine salt. Surfactant compositions were prepared by combining Guerbet alcohol surfactant at 3.33% and T/Am 5 at 6.66% in aqueous solution. These surfactant compositions were tankmixed with glyphosate at two glyphosate/surfactant ratios (2:1 and 4:1) and compared to a standard formulation and to a T/Am 5+blend at the same tankmix ratios. The Guerbet alcohol surfactants were G1 and G2 of Example 7.

The following procedures were followed. Velvetleaf and barnyardgrass (Japanese millet) were planted in standard 4 inch pots which contained a 50% mixture of Metro Mix and 50% Dupo silt loam soil. This soil mix was previously steam sterilized and prefertilized with Osmocote (14-14-14) slow release fertilizer at a rate of 100 gm per cubic foot. Approximately one week after emergence any unhealthy or extra plants were removed to create a uniform test pot prior to herbicide application. Herbicide applications were made via a track sprayer. The standard formulation used in this test was the commercial product Roundup® herbicide as sold in Canada, as described above. All pots were then placed in a warm supplemental lighted (approx. 475 microeinsteins) greenhouse and subirrigated to maintain adequate soil moisture for the duration of the test.

| Che | TRT | Formulation | Glyphosate Lb. ae/ Acre | Ratio Gly: Surf | % Inhibition 20 DAT (avg. 4 reps.) velvet- leaf | Barn- yard |
|---|---|---|---|---|---|---|
| 1 | 1 | Untreated | 0 |  | 0 | 0 |
|  | 2 | Roundup | 0.125 |  | 36.3 | 62.5 |
|  | 3 | Roundup | 0.25 |  | 57.5 | 78.8 |
|  | 4 | Roundup | 0.38 |  | 72.5 | 95.8 |
| 2 | 5 | Glyphosate + G1 + T/Am 5 | 0.125 | 2:1 | 33.8 | 65.0 |
|  | 6 | Glyphosate + G1 + T/Am 5 | 0.25 | 2:1 | 47.5 | 81.3 |
|  | 7 | Glyphosate + G1 + T/Am 5 | 0.38 | 2:1 | 73.8 | 93.3 |
|  | 8 | Glyphosate + G1 + T/AM 5 | 0.125 | 4:1 | 10.0 | 42.5 |
|  | 9 | Glyphosate + G1 + T/AM 5 | 0.25 | 4:1 | 37.5 | 67.5 |
|  | 10 | Glyphosate + G1 + T/AM 5 | 0.38 | 4:1 | 57.5 | 78.8 |
| 3 | 11 | Glyphosate + G2 + T/Am 5 | 0.125 | 2:1 | 31.3 | 62.5 |
|  | 12 | Glyphosate + G2 + T/Am 5 | 0.25 | 2:1 | 56.3 | 75.0 |
|  | 13 | Glyphosate + G2 + T/Am 5 | 0.38 | 2:1 | 66.3 | 95.3 |
|  | 14 | Glyphosate + G2 + T/Am 5 | 0.125 | 4:1 | 26.3 | 47.5 |
|  | 15 | Glyphosate + G2 + T/Am 5 | 0.25 | 4:1 | 43.8 | 75.0 |
|  | 16 | Glyphosate + G2 + T/Am 5 | 0.38 | 4:1 | 58.8 | 80.0 |

-continued

| Che | TRT | Formulation | Glyphosate Lb. ae/ Acre | Ratio Gly: Surf | % Inhibition 20 DAT (avg. 4 reps.) velvet- leaf | Barn- yard |
|---|---|---|---|---|---|---|
| 4 | 17 | Glyphosate + S/A19 + T/Am 5 | 0.125 | 2:1 | 32.5 | 51.3 |
|   | 18 | Glyphosate + S/A19 + T/Am 5 | 0.25 | 2:1 | 56.3 | 68.8 |
|   | 19 | Glyphosate + S/A19 + T/Am 5 | 0.38 | 2:1 | 67.5 | 88.8 |
|   | 20 | Glyphosate + S/A19 + T/Am 5 | 0.125 | 4:1 | 26.3 | 35.0 |
|   | 21 | Glyphosate + S/A19 + T/Am 5 | 0.25 | 4:1 | 45.0 | 71.3 |
|   | 22 | Glyphosate + S/A19 + T/Am 5 | 0.38 | 4:1 | 61.3 | 77.5 |

Example 9

A series of concentrated formulations were prepared containing 24 percent glyphosate as the isopropylamine salt of glyphosate and a mixture of a Guerbet alcohol (G3) of the formula of Example 7 with T/Am5. The ratio of G3 of T/Am5 varied from about 2:1 to about 8:1. The cloud point of the compositions were determined to range from 57 degrees C. to 86 degrees C. The highest cloud points were obtained with the highest ratios of T/Am 5/G3 ratios. However, all compositions were satisfactory with respect to practical utility with respect to this aspect of the concentrate compositions.

While the illustrative embodiments of the invention have been described with particularity, it will be understood that various other modifications will be apparent to and can readily be made by one of skin in the art without departing from the spirit and scope of the invention.

What is claimed is:

1. A storage-stable, liquid or water soluble dry concentrate agriculturally acceptable water soluble composition comprising:

(a) glyphosate or one or more of its salts or mixtures thereof;

(b) one or more alcohol surfactants having the following chemical structure

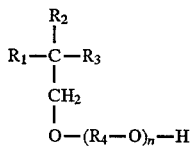

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups and n is an average number from about 3 to about 30; and (c) one or more other surfactants.

2. The composition of claim 1 wherein, in the structure of said alcohol surfactant, $R_1$ and $R_2$ are both straight chain alkyl groups with a total of about 7 to about 30 carbon atoms, $R_3$ is hydrogen and $R_4$ groups are ethylene.

3. The composition of claim 2 wherein, in the structure of said alcohol surfactant, n is an average number from about 7 to about 14.

4. The composition of claim 1 wherein said alcohol surfactant is an ethoxylated Guerbet alcohol having an alkyl moiety of about 12 to about 16 carbon atoms, and n is an average number from about 7 to about 14.

5. The composition of claim 1 wherein one or more other surfactant(s) are selected from the group consisting of alkyl monoglycosides, alkyl polyglycosides, sucrose alkylesters, tertiary and quaternary alkylamine alkoxylates, non-alkoxylated tertiary and quaternary alkylamines, alkylamine oxides and alkylbetaines.

6. The composition of claim 4 wherein said other surfactant comprises a tertiary alkylamine surfactant with about 2 to about 10 moles of ethylene oxide per mole of amine.

7. The composition of claim 6 wherein said tertiary alkylamine surfactant is a cocoamine or tallowamine with about 2 to about 5 moles of ethylene oxide per mole of amine.

8. The composition of claim 1 which is an aqueous concentrate formulation with a glyphosate acid equivalent loading in the range from about 5 to about 40 percent by weight.

9. The composition of claim 1 wherein which is a dry concentrate composition with glyphosate acid equivalent loading in the range from about 10 to about 75 percent by weight.

10. The composition of claim 1 which is a water-soluble granular formulation with a glyphosate acid equivalent loading in the range from about 40 to about 70 percent by weight.

11. The composition of claim 7 wherein the weight ratio of said alcohol surfactant to glyphosate acid equivalent is in the range of about 1:20 to about 1:1.

12. The composition of claim 11 wherein the weight ratio of said alcohol surfactant to glyphosate acid equivalent is in the range from about 1:12 to 1:2.

13. The composition of claim 12 wherein the weight ratio of said alcohol surfactant to glyphosate acid equivalent is in the range from about 1:6 to about 1:3.

14. The composition of claim 7 wherein the weight ratio of said alcohol surfactant to said tertiary alkylamine surfactant is in the range from about 1:20 to about 5:1.

15. The composition of claim 14 wherein the ratio is about 1:10 to about 2:1.

16. The composition of claim 14 wherein the ratio is about 1:5 to about 1:1.

17. An aqueous herbicidal spray solution comprising:

(a) glyphosate or one or more of its salts or mixtures thereof;

(b) one or more alcohol surfactants having the following chemical structure

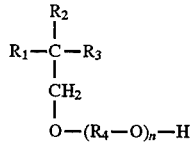

wherein $R_1$ and $R_2$ are independently straight or branched chain $C_1$ to about $C_{28}$ alky, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups and n is an average number from about 3 to about 30; and (c) one or more other surfactants; and (d) water.

18. The composition of claim 17 wherein, in the structure of said alcohol surfactant, $R_1$ and $R_2$ are both straight chain alkyl groups with a total of about 7 to about 30 carbon atoms, $R_3$ is hydrogen and $R_4$ groups are ethylene.

19. The composition of claim 18 wherein, in the structure of said alcohol surfactant, n is an average number from about 7 to about 14.

20. The composition of claim 17 wherein said alcohol surfactant is an ethoxylated Guerbet alcohol having an alkyl moiety of about 12 to about 16 carbon atoms, and n is an average number from about 7 to about 14.

21. The composition of claim 17 wherein one or more other surfactant(s) are selected from the group consisting of alkyl monoglycosides, alkyl polyglycosides, sucrose alkylesters, tertiary and quaternary alkylamine alkoxylates, non-alkoxylated tertiary and quaternary alkylamines, alkylamine oxides and alkylbetaines.

22. The composition of claim 21 wherein said other surfactant comprises a tertiary alkylamine surfactant with about 2 to about 10 moles of ethylene oxide per mole of amine.

23. The composition of claim 17 wherein said tertiary alkylamine surfactant is a cocoamine or tallowamine with about 2 to about 5 moles of ethylene oxide per mole of amine.

24. The composition of claim 23 wherein the weight ratio of said alcohol surfactant to glyphosate acid equivalent is in the range of about 1:20 to about 1:1.

25. The composition of claim 23 wherein the weight ratio of said alcohol surfactant to glyphosate acid equivalent is in the range from about 1:12 to 1:2.

26. The composition of claim 23 wherein the weight ratio of said alcohol surfactant to glyphosate acid equivalent is in the range from about 1:6 to about 1:3.

* * * * *